United States Patent [19]

Draber et al.

[11] 4,067,724
[45] Jan. 10, 1978

[54] N-(1,2,4-TRIAZIN-5-ON-4-YL)-GLYCINES AND HERBICIDAL COMPOSITIONS

[75] Inventors: Wilfried Draber, Wuppertal; Karlfried Dickore, Leverkusen; Helmut Timmler, Wuppertal; Ludwig Eue, Leverkusen; Robert Rudolf Schmidt, Cologne, all of Germany

[73] Assignee: Bayer Aktiengesellschaft, Leverkusen, Germany

[21] Appl. No.: 717,715

[22] Filed: Aug. 25, 1976

[30] Foreign Application Priority Data

Sept. 13, 1975 Germany .............................. 2540958
May 8, 1976 Germany .............................. 2620370

[51] Int. Cl.$^2$ ...................... C07D 253/06; A01N 9/22
[52] U.S. Cl. ......................................... 71/93; 544/182
[58] Field of Search ...................... 260/248 AS; 71/93

[56] References Cited

U.S. PATENT DOCUMENTS 3,966,715  6/1976  Westphil et al. .......... 260/248 AS X Primary Examiner—John M. Ford
Attorney, Agent, or Firm—Burgess, Dinklage & Sprung

[57] ABSTRACT

N-(1,2,4-Triazin-5-on-4-yl)-glycine compounds of the formula

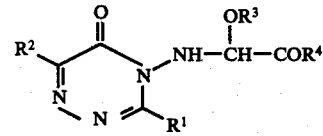

in which
R$^1$ is alkyl, alkoxy, alkylthio or alkylamino,
R$^2$ is alkyl, cycloalkyl, phenyl or substituted phenyl,
R$^3$ is hydrogen, alkyl, alkenyl or alkynyl and
R$^4$ is hydroxyl, alkoxy, alkythio, amino, alkylamino or dialkylamino, possess outstanding selective herbicidal properties.

26 Claims, No Drawings

N-(1,2,4-TRIAZIN-5-ON-4-YL)-GLYCINES AND HERBICIDAL COMPOSITIONS

The present invention relates to certain new N-(1,2,4-triazin-5-on-4-yl)-glycine compounds, to herbicidal compositions containing them, and to their use of herbicides.

It is known that 1,2,4-triazin-5-one derivatives, for example 4-amino-6-tert.-butyl-3-methylthio-1,2,4-triazin-5-one or 4-amino-6-phenyl-3-methylthio-1,2,4-triazin-5-one, can be employed as herebicides, from U.S. Pat. No. 3,671,523 and German Offenlegungsschrift (German Published Specification) 1,542,873. While these compounds are herbicidally highly active, they are unsuitable for use as selective herbicides in some crop cultures since they can cause substantial damage when used in fairly high amounts.

The invention provides N-(1,2,4-triazin-5-on-4-yl)-glycine derivaties of the general formula

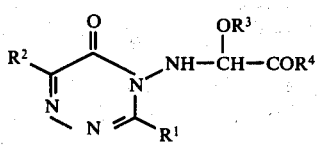

in which
R$^1$ is alkyl, alkoxy, alkylthio or alkylamino,
R$^2$ is alkyl, cycloalkyl, phenyl or substituted phenyl,
R$^3$ is hydrogen, alkyl, alkenyl or alkynyl and
R$^4$ is hydroxyl, alkoxy, alkythio, amino, alkylamino or dialkylamino.

Preferably, R$^1$ is straight-chain or branched alkyl, alkoxy or alkylthio, each of from 1 to 4 carbon atoms, or alkylamino of from 2 to 4 carbon atoms, R$^2$ is straight chain or branched alkyl of from 1 to 6 carbon atoms (especially tert.-butyl), cycloalkyl of from 5 to 7 carbon atoms, or optionally substituted phenyl, preferred possible substituents being halogen (especially chlorine and bromine), alkyl or alkoxy each of 1 or 2 carbon atoms, haloalkyl of from 2 to 5 halogen atoms, especially fluorine, and 1 or 2 carbon atoms, cyano or nitro, R$^3$ is hydrogen, alkyl of from 1 to 4 carbon atoms, or alkenyl or alkynyl, each of from 2 to 4 carbon atoms, and R$^4$ is hydroxyl, alkoxy or alkylthio each of from 1 to 4 carbon atoms, especially methoxy or ethoxy, amino or alkylamino or dialkylamino of from 1 to 4, especially 1 or 2, carbon atoms in each alkyl moiety.

Surprisingly, the N-(1,2,4-triazin-5-on-4-yl)-glycine derivatives of the invention, while having an equally good total herbicidal action, show a substantially better selective activity in crops than do the known active compounds 4-amino-6-tert.-butyl-3-methylthio-1,2,4-triazin-5-one and 4-amino-6-phenyl-3-methylthio-1,2,4-triazin-5-one. The new active compounds according to the invention thus represent an enrichment of the art.

The invention also provides a process for the production of a N-(1,2,4-triazin-5-on-4-yl) derivative of the formula (I) in which a 4-amino-1,2,4-triazin-5-one of the formula

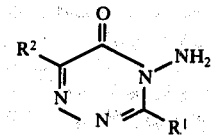

in which
R$^1$ and R$^2$ have the abovementioned meanings is reacted with glyoxylic acid or a glyoxylic acid derivative of the formula

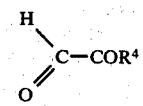

in which
R$^4$ has the abovementioned meaning and (in the case in which, in formula (I), R$^3$ is not hydrogen), additionally, with an alcohol of the formula

R$^5$OH  (IV)

in which
R$^5$ is alkyl, alkenyl or alkynyl, optionally in the presence of a diluent.

If 3-ethyl-4-amino-6-(3'-trifluoromethylphenyl)-1,2,4-triazin-5-one and glyoxylic acid are used as starting materials, the course of the reaction can be represented by the following formula scheme:

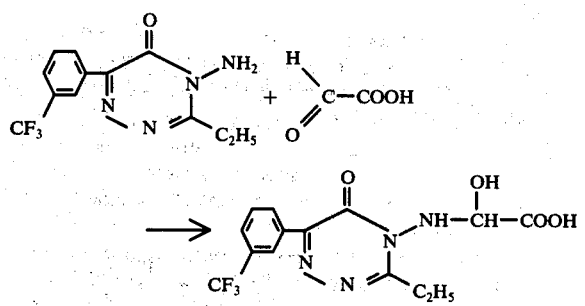

If 4-amino-6-tert.-butyl-3-methylthio-1,2,4-triazin-5-one, glyoxylic acid and ethanol are used as starting materials, the course of the reaction can be represented by the following formula:

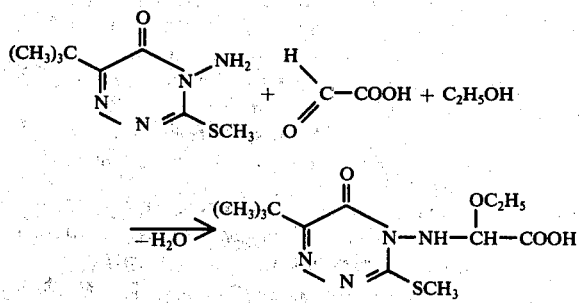

The formula (II) provides a general definition of the 4-amino-1,2,4-triazin-5-ones used as starting materials.

The following may be mentioned individually as examples of these starting materials: 4-amino-3-methoxy-6-methyl-1,2,4-triazin-5-one, 4-amino-3-methoxy-6-phenyl-1,2,4-triazin-5-one, 4-amino-3- methoxy-6-t.-butyl-1,2,4-triazin-5-one, 4-amino-3-methoxy-6-(4'-chlorophenyl)-1,2,4-triazin-5-one, 4-amino-3-methoxy-6-cyclohexyl-1,2,4-triazin-5-one, 4-amino-3-ethoxy-6-ethyl-1,2,4-triazin-5-one, 4-amino-3-ethoxy-6-t.-butyl-1,2,4-triazin-5-one, 4-amino-3-ethoxy-6-(4'-nitrophenyl)-1,2,4-triazin-5-one, 4-amino-3-butoxy-6-phenyl-1,2,4-triazin-5-one, 4-amino-3-methylthio-6-t.-butyl-1,2,4-triazin-5-one, 4-amino-3-methylthio-6-phenyl-1,2,4-triazin-5-one, 4-amino-3-methylthio-6-(3'-trifluoromethylphenyl)-1,2,4-triazin-5-one, 4-amino-3-methylthio-6-(2',4'-dichlorophenyl)-1,2,4-triazin-5-one, 4-amino-3-methylthio-6-cyclohexyl-1,2,4-triazin-5-one, 4-amino-3-ethylthio-6-methyl-1,2,4-triazin-5-one, 4-amino-3-ethylthio-6-t.-butyl-1,2,4-triazin-5-one, 4-amino-3-propylthio-6-t.-butyl-1,2,4-triazin-5-one, 4-amino-3-propylthio-6-phenyl-1,2,4-triazin-5-one, 4-amino-3-methyl-amino-6-methyl-1,2,4-triazin-5-one, 4-amino-3-methylamino-6-phenyl-1,2,4-triazin-5-one, 4-amino-3-methylamino-6-ethyl-1,2,4-triazin-5-one, 4-amino-3-methylamino-6-(4'-methylphenyl)-1,2,4-triazin-5-one, 4-amino-3-ethylamino-6-t.-butyl-1,2,4-triazin-5-one, 4-amino-3-propylamino-6-propyl-1,2,4-triazin-5-one, 4-amino-3-butylamino-6-(4'-nitrophenyl)-1,2,4-triazin-5-one, 4-amino-3-methyl-6-t.-butyl-1,2,4-triazin-5-one, 4-amino-3-methyl-6-i.-propyl-1,2,4-triazin-5-one, 4-amino-3-methyl-6-cyclohexyl-1,2,4-triazin-5-one, 4-amino-3-ethyl-6-phenyl-1,2,4-triazin-5-one, 4-amino-3-ethyl-6-(3'-trifluoromethylphenyl)-1,2,4-triazin-5-one, 4-amino-3-ethyl 6-ethyl-1,2,4-triazin-5-one, 4-amino-3-ethyl-6-t.-butyl-1,2,4-triazin-5-one, 4-amino-3-t.-butyl-6-t.-butyl-1,2,4-triazin-5-one and 4-amino-3-t.-butyl-6-phenyl-1,2,4-triazin-5-one.

Many of the 4-amino-1,2,4-triazin-5-ones of the formula (II) are known from U.S. Pat. No. 3,671,523 and German Offenlegungsschriften (German Published Specifications) 1,542,873, 2,107,757, 2,138,031 and 2,224,161. Compounds of the formula (II) not previously known can be prepared in a simple manner in accordance with processes previously described in the abovementioned literature.

The formula (III) provides a general definition of the glyoxylic acid derivatives to be used as starting materials.

The following may be mentioned individually as examples of these starting materials: glyoxylic acid, glyoxylic acid methyl ester, glyoxylic acid ethyl ester, glyoxylic acid propyl ester, glyoxylic acid butyl ester, glyoxylic acid thiomethyl ester, glyoxylic acid thioethyl ester, glyoxylic acid amide, glyoxylic acid methylamide, glyoxylic acid ethylamide, glyoxylic acid i-propylamide, glyoxlic acid dimethylamide, glyoxylic acid diethylamide, glyoxylic acid ethyl methylamide and glyoxylic acid methyl propylamide.

The glyoxylic acid derivatives of the formula (III) are compounds generally known in organic chemistry.

The formula (IV) provides a general definition of the alcohols which are also to be used as starting materials. In this formula, $R^5$ preferably represents alkyl of from 1 to 4 carbon atoms, or alkenyl or alkynyl, each of from 2 to 4 carbon atoms. The following may be mentioned individually as examples of these alcohols: methyl alcohol, ethyl alcohol, n-propyl alcohol, i-propyl alcohol, n-butyl alcohol, i-butyl alcohol, sec.-butyl alcohol, tert.-butyl alcohol, allyl alcohol and propargyl alcohol.

The alcohols of the formula (IV) used as starting materials are compounds which are generally known in organic chemistry and are easily accessible.

All inert solvents can be used as diluents for the reaction according to the invention. Preferred diluents include hydrocarbons, such as benzene, xylene and toluene; ethers, such as dioxan and tetrahydrofuran; esters, such as ethyl acetate and chlorinated hydrocarbons, such as chloroform and methylene chloride. In the case of compounds of the formula (I) in which $R^3$ is not hydrogen, an excess of the alcohol employed, of the formula (IV), is preferably used as the diluent.

The reaction temperatures can be varied over a substantial range. In general, the reaction is carried out at 10° to 50° C, preferably at room temperature.

In carrying out the process according to the invention, equimolar amounts may be used. In a particular embodiment of the process, 1 to 1.2 mole of the glyoxylic acid derivative of the formula (III), as the monohydrate or in the form of an aqueous solution, are employed per mol of 4-amino-1,2,4-triazin-5-one of the formula (II), and the alcohol of the formula (IV) is employed in a substantial excess, at the same time acting as solvent. The reaction products may be isolated in accordance with generally customary methods. A suitable procedure is that after completion of the reaction the mixture is filtered and the filtrate is concentrated in stages. The combined filter residues are washed or triturated in an organic solvent, and dried.

The following examples illustrate the preparation of the compounds of the present invention.

EXAMPLE 1

N-(3-methylthio-6-tert.-butyl-1,2,4-triazin-5-on-4-yl)-α-ethoxy-glycine

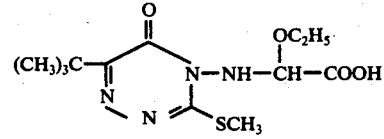

214 g (1 mol) of 4-amino-6-tert.-butyl-3-methylthio-1,2,4-triazin-5-one, 101 g (1.1 mols) of glyoxylic acid monohydrate and 2 liters of ethanol were stirred for 12 hours at room temperature. The product which had precipitated was filtered off and the filtrate was concentrated, whereupon further material crystallized out. The combined filtrate residues were stirred in about 500 ml of cold water for ½ hour and the product was filtered off and dried at 40° C in vacuo. 304 g (96% of theory) of N-(3-methylthio-6-tert.-butyl-1,2,4-triazin-5-on-4-yl)-α-ethoxy-glycine of melting point 154°–55° C (decomposition) were obtained.

EXAMPLE 2

N-(3-methylthio-6-tert.-butyl-1,2,4-triazin-5-on-4-yl)-α-hydroxy-glycine

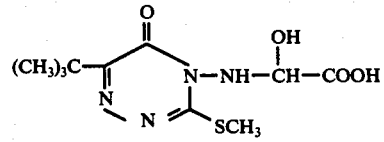

21.4 g (0.1 mol) of 4-amino-6-tert.-butyl-3-methylthio-1,2,4-triazin-5-one and 10.1 g (0.11 mol) of glyoxylic acid monohydrate were stirred in 250 ml of ethyl acetate for 12 hours at room temperature, whereby a clear solution was produced. The mixture was then left to stand; after about 3 hours, the product began to crystallize out. It was filtered off and the filtrate was concentrated, whereupon further material crystallized out. The combined filter residues were washed with ether and dried. 25.2 g (87.5% of theory) of N-(3-methylthio-6-tert.-butyl-1,2,4-triazin-5-on-4-yl)- α-hydroxy-glycine of melting point 161° C (decomposition) were obtained.

EXAMPLE 3 – 31

The compounds listed in Table 1 which follows are obtained by methods analgous to those of Examples 1 and 2.

Table 1

$$R^2 \underset{\underset{N}{\overset{N}{\diagdown}}\underset{N}{\diagup}}{\overset{\overset{O}{\|}}{C}} N-NH-\underset{\underset{R^1}{|}}{\overset{OR^3}{\underset{|}{CH}}}-COR^4 \quad (I)$$

| Example No. | $R^1$ | $R^2$ | $R^3$ | $R^4$ | Melting point (° C) |
|---|---|---|---|---|---|
| 3 | —CH(CH$_3$)$_2$ | t-C$_4$H$_9$ | C$_2$H$_5$ | OH | 119 (decomposition) |
| 4 | CH$_3$ | C$_6$H$_5$ | C$_2$H$_5$ | OH | 138 (decomposition) |
| 5 | CH$_3$ | C$_6$H$_5$ | CH$_3$ | OH | 134 |
| 6 | CH$_3$ | C$_6$H$_5$ | n-C$_4$H$_9$ | OH | 116–17 |
| 7 | SCH$_3$ | t-C$_4$H$_9$ | CH$_3$ | OH | 149–50 (decomposition) |
| 8 | CH$_3$ | C$_6$H$_5$ | —CH$_2$C≡CH | OH | 119–21 (decomposition) |
| 9 | SCH$_3$ | t-C$_4$H$_9$ | C$_2$H$_5$ | OC$_2$H$_5$ | Oil |
| 10 | C$_2$H$_5$ | 3-CF$_3$—C$_6$H$_4$ | C$_2$H$_5$ | OH | 125 (decomposition) |
| 11 | C$_2$H$_5$ | 3-CF$_3$—C$_6$H$_4$ | CH$_3$ | OH | 130 (decomposition) |
| 12 | SCH$_3$ | t-C$_4$H$_9$ | —CH(CH$_3$)$_2$ | OH | 138–40 |
| 13 | CH$_3$ | C$_6$H$_5$ | H | OH | 104 (decomposition) |
| 14 | OCH$_3$ | C$_6$H$_5$ (phenyl) | H | OH | 142 (decomp.) |
| 15 | SCH$_3$ | C$_6$H$_5$ (phenyl) | H | OH | 161 (decomp.) |
| 16 | SC$_2$H$_5$ | C$_6$H$_5$ (phenyl) | H | OH | 127 (decomp.) |
| 17 | SCH$_3$ | i-C$_3$H$_7$ | CH$_3$ | OH | 150 (decomp.) |
| 18 | SCH$_3$ | s-C$_4$H$_9$ | CH$_3$ | OH | 148 (decomp.) |
| 19 | SCH$_3$ | s-C$_4$H$_9$ | C$_2$H$_5$ | OH | 118 (decomp.) |
| 20 | SCH$_3$ | s-C$_4$H$_9$ | CH$_3$ | OCH$_3$ | viscous oil |
| 21 | C$_2$H$_5$ | t.-C$_4$H$_9$ | CH$_3$ | OH | 128 (decomp.) |
| 22 | i-C$_3$H$_7$ | t.-C$_4$H$_9$ | CH$_3$ | OH | 162 (decomp.) |
| 23 | SCH$_3$ | t.-C$_4$H$_9$ | CH$_3$ | OCH$_3$ | viscous oil |
| 24 | i-C$_3$H$_7$ | t.-C$_4$H$_9$ | C$_2$H$_5$ | OCH$_3$ | viscous oil |
| 25 | i-C$_3$H$_7$ | t.-C$_4$H$_9$ | CH$_3$ | OCH$_3$ | viscous oil |
| 26 | SCH$_3$ | t.-C$_4$H$_9$ | i-C$_3$H$_7$ | OCH$_3$ | viscous oil |
| 27 | SCH$_3$ | (CH$_3$)$_2$CH—CH(CH$_3$)— | CH$_3$ | OH | 153 (decomp.) |
| 28 | SCH$_3$ | C$_3$H$_7$—CH(CH$_3$)— | CH$_3$ | OH | 151 (decomp.) |
| 29 | SCH$_3$ | (C$_2$H$_5$)$_2$CH | CH$_3$ | OH | 153 (decomp.) |
| 30 | SCH$_3$ | cyclopentyl | CH$_3$ | OH | 144 (decomp.) |
| 31 | SCH$_3$ | H | CH$_3$ | OH | 165 (decomp.) |

The active compounds according to the invention influence plant growth and can therefore be used as defoliants, desiccants, agents for destroying broadleaved plants and germination inhibitors and especially as weed-killers. Weeds in the broadest sense are to be understood as all plants which grow in locations where they are not desired. Whether the compounds according to the invention act as total or selective herbicides depends essentially on the amount used.

The active compounds according to the invention can be used, for example, in the case of the following plants:

*Dicotyledon weeds* of the genera: mustard (Sinapis), cress (Lepidium), bed straw (Galium), chickweed (Stellaria), camomile (Matricaria), mayweed (Anthemis), gallant soldier (Galinsoga), goosefoot (Chenopodium), annual nettle (Urtica), groundsel (Senecio), pigweed (Amaranthus), purslane (Portulaca), cocklebur (Xanthium), bindweed (Convolvulus), morning glory (Ipomoea), knotweed (Polygonum), sesbania (Sesbania), ragweed (Ambrosia), spear thistle (Cirsium), common thistle (Carduus), sow thistle (Sonchus), nightshade (Solanum), field cress (Rorippa), toothcup (Rotala), (Lindernia), deadnettle (Lamium), speedwell (Veronica), mallow (Abutilon), emex (Emex), thornapple (Datura), violet (Viola), hemp-nettle (Galeopsis), poppy (Papaver) and knapweed (Centaurea).

*Dicotyledon cultures* of the genera: cotton (Gossypium), soya bean (Glycine); beet (Beta), carrot (Daucus), bean (Phaseolus), pea (Pisum), potato (Solanum), flax (Linum), morning glory (Ipomoea), broad bean (Vicia), tobacco (Nicotiana), tomato (Lycopersicon), groundnut (Arachis), cabbage (Brassica), lettuce (Lactuca), cucumber (Cucumis) and marrow (Cucurbita).

*Monocotyledon weeds* of the genera: barnyard grass (Echinochloa), foxtail (Setaria), wild millet (Panicum), crabgrass (Digitaria), timothy (Phleum), bluegrass (Poa), fescue (Festuca), goosegrass (Eleusine), signalgrass (Brachiaria), ryegrass (Lolium), cheat (Bromus), oats (Avena), flatsedge (Cyperus), sorghum (Sorghum), quackgrass (Agropyron), Bermuda grass (Cynodon), Monocharia, fimbristylis, (Fimbristylis), arrowhead (Sagittaria), spikerush (Eleocharis), bulrush (Scirpus), paspalum (Paspalum), Ischaemum, gooseweed (Sphenoclea), crowfoot grass (Dactyloctenium), redtop (Agrostis), meadow foxtail (Alopecurus) and silky bentgrass (Apera).

*Monocotyledon cultures* of the genera: rice (Oryza), maize (Zea), wheat (Triticum), barley (Hordeum), oats (Avena), rye (Secale), sorghum (Sorghum), millet (Panicum), sugar cane (Saccharum), pineapple (Ananas), asparagus (Asparagus) and leek (Allium).

The use of the active compounds according to the invention is in no way restricted to these genera but also extends, in the same way, to other plants.

Depending on the concentration, the compounds are suitable for the total combating of weeds, for example on industrial terrain and rail tracks, and on paths and squares with or without trees. The compounds can equally be used for combating weeds in perennial cultures, for example afforestation, decorative tree plantings, orchards, vineyards, citrus plantations, nut plantings, banana plantations, coffee plantations, tea plantations, rubber plantations, oil palm plantations, cocoa plantations, soft fruit plantings and hop fields, and for the selective combating of weeds in annual cultures.

Their use as a selective agent for combating weeds in standing crop plant cultivations, such as soy beans, potatoes, cereals, for example barley, oats, wheat and maize, as well as rice and beet, should be mentioned particularly.

The active compounds according to the present invention can be converted into the usual formulations, such as solutions, emulsions, suspensions, powders, pastes and granulates. These may be produced in known manner, for example by mixing the active compounds with extenders, that is, liquid or solid or liquefied gaseous diluents or carriers, optionally with the use of surface-active agents, that is, emulsifying agents and/or dispersing agents, and/or foam-forming agents. In the case of the use of water as an extender, organic solvents can, for example, also be used as auxiliary solvents.

As liquid diluents or carriers, there are preferably used aromatic hydrocarbons, such as xylenes, toluene, benzene or alkyl naphthalenes, chlorinated aromatic or aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethyl formamide, dimethyl sulfoxide or acetonitrile, as well as water.

As liquefied gaseous diluents or carriers are meant liquids which would be gaseous at normal temperatures and pressures, e.g., aerosol propellants, such as halogenated hydrocarbons, e.g. freon.

As solid diluents or carriers, there are preferably used ground natural minerals, such as kaolins, clays, talc, chalk, quartz, attapulgite, montmorillonite or diatomaceous earth, or ground synthetic minerals, such as highly-dispersed silicic acid, alumina or silicates.

Preferred examples of emulsifying and foam-forming agents include non-ionic and anionic emulsifiers, such as polyoxyethylene-fatty acid esters, polyoxyethylene-fatty alcohol ethers, for example alkylarylpolyglycol ethers, alkyl sulfonates, alkyl sulfates and aryl sulfonates as well as albumin hydrolyzation products; and preferred examples of dispersing agents include lignin-sulfate waste liquors and methyl cellulose.

The active compounds according to the invention, as such or in their formulations, can (in order to reinforce and supplement their spectrum of action in accordance with the intended use) be combined with other herbicidal active compounds, it being possible to use finish formulations or tank mixing. In particular, the active compounds mentioned below, and other representatives of the groups of active compounds characterized by these active compounds, are suitable for such combination.

2,3,6-Trichlorobenzoic acid and its salts, 2,3,5,6-tetrachlorobenzoic acid and its salts, 3-nitro-2,3-dichlorobenzoic acid and its salts, 3-amino-2,5-dichlorobenzoic acid and its salts, 2-methoxy-3,6-dichlorobenzoic acid and its salts, 2-methoxy-3,5,6-trichlorobenzoic acid and its salts, 2,6-dichloro-thiobenzamide, 2,6-dichlorobenzonitrile, 2,4-dichlorophenoxyacetic acid and its salts and esters, 2,4,5-trichlorophenoxyacetic acid and its salts and esters, (2-methyl-4-chlorophenoxy)-acetic acid and its salts and esters, 2-(2,4-dichlorophenoxy)-propionic acid, 2-(2-methyl-4-chlorophenoxy)-propionic acid and 2-(2,4,5-trichlorophenoxy)-propionic acid and their salts and esters, 4-(2,4-dichlorophenoxy)-butyric acid and its salts and esters, 4-(2-methyl-4-chlorophenoxy)-butyric acid and its salts and esters, 2,3,6-trichlorophenyl-acetic acid and its salts and 4-amino-3,5,6-trichloropicolinic acid.

Trichloroacetic acid and its salts, 2,2-dichloropropionic acid and its salts, 2-chloro-N,N-diallylacetic acid amide, dinitrocresol, dinitro-sec.-butylphenol and its salts.

3-Phenyl-1,1-dimethyl-urea, 3-(4'-chlorophenyl)-1,1-dimethyl-urea, 3-(3',4'-dichlorophenyl)-1,1-dimethyl-urea, 3-(3',4'-dichlorophenyl)-1-n-butyl-1-methyl-urea, 3-(3',4'-dichlorophenyl)-1,1,3-trimethyl-urea, 3-(4'-chlorophenyl)-1-methoxy-1-methyl-urea, 3-(3'-trifluoromethyl-phenyl)-1,1-dimethyl-urea, 3-(3',4'-dichlorophenyl)-1-methoxy-1-methyl-urea, 3-(4'-bromophenyl)-1-methoxy-1-methyl-urea, 3-(3',4'-dichlorophenyl)-3-methoxy-1,1-dimethyl-urea, 3-(4'-chlorophenoxyphenyl)-1,1-dimethyl-urea, N'-cyclooctyl-N,N-dimethyl-urea, 3-(benzthiazol-2-yl)-1,3-dimethylurea and 3-(3-chloro-4-methylphenyl)-1,1-dimethylurea.

N,N-Di-(n-propyl)-S-n-propyl-thiocarbamic acid ester, N-ethyl-N-(n-butyl)-S-n-propyl-thiocarbamic acid ester, N,N-di-(n-propyl)-S-ethyl-thiocarbamic acid ester, N-phenyl-O-isopropyl-carbamic acid ester, N-(m-chlorophenyl)-O-isopropylcarbamic acid ester, N-(3',4'-dichlorophenyl)-O-methylcarbamic acid ester, N-(m-chlorophenyl)-O-(4-chloro-butin-2-yl)-carbamic acid ester, N-(3'-methylphenyl)O-(3-methoxycarbonylaminophenyl)-carbamic acid ester and N,N-diisopropylthiocarbamic acid 2,3,3-trichloroallyl ester.

3-Cyclohexyl-5,6-trimethylene-uracil, 5-bromo-3-sec.-butyl-6-methyl-uracil, 3,6-dioxo-1,2,3,6-tetrahydropyridazine and 4-amino-5-chloro-1-phenyl-6-pyridazone.

2-Chloro-4-ethylamino-6-isopropylamino-s-triazine, 2-chloro-4,6-bis-(methoxypropylamino)-s-triazine, 2-methoxy-4,6-bis-(isopropylamino)-s-triazine, 2-diethylamino-4-isopropylacetamido-6-methoxy-s-triazine, 2-isopropylamino-4-methoxypropylamino-6-methylthio-s-triazine, 2-methylthio-4,6-bis-(isopropylamino)-s-triazine, 2-chloro-4,6-bis-(ethylamino)-s-triazine, 2-methylthio-4,6-bis-(ethylamino)-s-triazine, 2-methoxy-4-ethylamino-6-isopropylamino-s-triazine, 2-methylthio-4-ethylamino-6-isopropylamino-s-triazine, 2-methoxy-4,6-bis-(ethylamino)-s-triazine and 2-chloro-4,6-bis-(isopropylamino)-s-triazine.

N,N-Diethyl-2,4-dinitro-6-trifluoromethyl-1,3-phenylenediamine, N,N-di-n-propyl-2,6-dinitro-4-trifluoromethyl-aniline, 4'-nitro-2,4-dichloro-diphenyl ether, 3,4-dichlorophenyl-propionamide and 2',6'-diethyl-N-(methoxymethyl)-2-chloroacetanilide.

The active compounds according to the invention can be used as a mixture with other active compounds, such as fungicides, insecticides and acaricides.

The formulations in general contain 0.1 to 95 percent by weight of active compound, preferably 0.5 to 90 percent by weight.

The active compounds can be used as such, in the form of their formulations or in the application forms prepared therefrom, such as ready-to-use solutions, emulsions, suspensions, powders, pastes and granulates. They can be applied in the customary manner, for example by spraying, atomizing, dusting, scattering and watering.

The compositions may be diluted for actual application, and the amount of active compound used can vary within substantial ranges. It depends essentially on the nature of the desired effect. In general, the active compound is applied to an area of agriculture in an amount of 0.1 to 20 kg per ha, preferably 0.2 to 15 kg/ha. When the compound is used as a selective herbicide, as described above, the amount may be appropriately selected within these ranges.

The compounds can be used both in accordance with the post-emergence method and in accordance with the pre-emergence method.

The invention therefore provides a herbicidal composition containing as active ingredient a compound according to the invention in admixture with a solid or liquefied gaseous diluent or carrier or in admixture with a liquid diluent or carrier containing a surface-active agent.

The invention also provides a method of combating weed pests which comprises applying to the pests or a habitat thereof a compound according to the invention alone or in the form of a composition containing as active ingredient a compound according to the invention in admixture with a diluent or carrier.

The invention also provides means of yielding crops protected from damage by weeds by being grown in areas in which, immediately prior to and/or during the time of the growing, a compound according to the invention was applied alone or in admixture with a diluent or carrier. It will be seen that the usual methods of providing a harvested crop may be improved by the present invention.

The compounds according to the invention, and the preparation and use of the compounds according to the invention, are illustrated by the following Examples.

Example A

Post-emergence test

Solvent: — 5 parts by weight of acetone

Emulsifier: — 1 part by weight of alkylaryl polyglycol ether

To produce a suitable preparation of active compound, 1 part by weight of active compound was mixed with the stated amount of solvent, the stated amount of emulsifier was added and the concentrate was then diluted with water to the desired concentration.

Test plants which had a height of 5–15 cm were sprayed with the preparation of the active compound in such a way as to apply the amounts of active compound per unit area which are indicated in the table. The concentration of the spray liquor was so chosen that the amounts of active compound shown in the table were applied in 2,000 liters of water/ha. After three weeks, the degree of damage to the plants was rated in % damage in comparison to the development of the untreated control. The figures denote:

0% = no action (like untreated control)

100% = total destruction.

The active compounds, the amounts applied and the results can be seen from the table which follows:

Table A

| Active compound | Amount of active compound used, kg/ha | Post-emergence Test Potatoes | Avena fatua | Amaranthus retroflexus | Chenopodium album |
|---|---|---|---|---|---|
| $(CH_3)_3C$ — [triazinone with N—NH₂, SCH₃] (known) | 3<br>2<br>1 | 30<br>20<br>0 | 100<br>100<br>100 | 100<br>100<br>100 | 100<br>100<br>100 |
| $(CH_3)_3C$ — [triazinone with N—NH—CH(OC₂H₅)—CO₂H, SCH₃] (1) | 3<br>2<br>1 | 0<br>0<br>0 | 100<br>100<br>100 | 100<br>100<br>100 | 100<br>100<br>100 |
| $(CH_3)_3C$ — [triazinone with N—NH—CH(OCH₃)—CO₂H, SCH₃] (7) | 3<br>2<br>1 | 0<br>0<br>0 | 100<br>100<br>100 | 100<br>100<br>100 | 100<br>100<br>100 |

Example B

Pre-emergence Test
Solvents: — 5 parts by weight acetone
Emulsifier: — 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

Seeds of the test plants were sown in normal soil and, after 24 hours, watered with the preparation of the active compound. It was expedient to keep constant the amount of water per unit area. The concentration of the active compound in the preparation was of no importance, only the amount of active compound applied per unit area being decisive. After three weeks, the degree of damage to the plants was determined in % damage in comparison to the development of the untreated control. The figures denote:

0% = no action (like untreated control)
100% = total destruction

The active compounds, the amounts applied and the results can be seen from the table which follows:

Table B₁

| Active compound | Amount of active compound used, kg/ha | Soya beans | Maize | Potatoes | Avena fatua | Echinochloa crus galli | Digitaria spec. | Amaranthus retrofl. | Chenopodium album |
|---|---|---|---|---|---|---|---|---|---|
| $(CH_3)_3C$ — [triazinone with N—NH₂, SCH₃] (known) | 2.5<br>1.25<br>0.625 | 20<br>0<br>0 | 50<br>30<br>10 | 10<br>0<br>0 | 100<br>100<br>100 | 100<br>100<br>100 | 100<br>100<br>100 | 100<br>100<br>100 | 100<br>100<br>100 |
| $(CH_3)_3C$ — [triazinone with N—NH—CH(OC₂H₅)—CO₂H, SCH₃] (1) | 2.5<br>1.25<br>0.625 | 10<br>0<br>0 | 0<br>0<br>0 | 0<br>0<br>0 | 100<br>100<br>100 | 100<br>100<br>100 | 100<br>100<br>100 | 100<br>100<br>100 | 100<br>100<br>100 |
| $(CH_3)_3C$ — [triazinone with N—NH—CH(OCH₃)—CO₂H, SCH₃] (7) | 2.5<br>1.25<br>0.625 | 10<br>0<br>0 | 0<br>0<br>0 | 0<br>0<br>0 | 100<br>100<br>100 | 100<br>100<br>100 | 100<br>100<br>100 | 100<br>100<br>100 | 100<br>100<br>100 |

Table B₁-continued

Pre-emergence Test

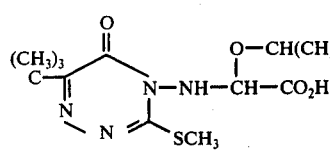

| | | | Pre-emergence Test | | | | | | | |
|---|---|---|---|---|---|---|---|---|---|---|
| (CH₃)₃C structure with O—CH(CH₃)₂ | | 2.5 | 0 | 5 | 0 | 100 | 100 | 100 | 100 | 100 |
| | | 1.25 | 0 | 0 | 0 | 100 | 100 | 100 | 100 | 95 |
| | | 0.625 | 0 | 0 | 0 | 95 | 100 | 100 | 100 | 90 |

(12)

| Active compound (=Example No.) | Amount of active compound used, kg/ha | Soya beans | Maize | Avena fatua | Echinochloa crus galli | Digitaria spec. | Amaranthus retroflexus | Chenopodium album |
|---|---|---|---|---|---|---|---|---|
| 18 | 2,5 | 40 | 90 | 100 | 100 | 100 | 100 | 100 |
| | 1,25 | 20 | 70 | 100 | 100 | 100 | 100 | 100 |
| | 0,625 | 0 | 0 | 100 | 100 | 100 | 100 | 100 |
| 19 | 2,5 | 100 | 40 | 100 | 100 | 100 | 100 | 100 |
| | 1,25 | 80 | 20 | 100 | 100 | 100 | 100 | 100 |
| | 0,625 | 30 | 0 | 100 | 100 | 100 | 100 | 100 |
| 15 | 2,5 | 0 | 0 | 80 | 80 | 100 | 100 | 100 |
| | 1,25 | 0 | 0 | 60 | 60 | 100 | 100 | 100 |
| | 0,625 | 0 | 0 | 60 | 60 | 100 | 100 | 100 |
| 22 | 2,5 | 90 | 20 | 100 | 100 | 100 | 100 | 100 |
| | 1,25 | 40 | 0 | 100 | 100 | 100 | 100 | 100 |
| | 0,625 | 0 | 0 | 100 | 100 | 100 | 100 | 100 |
| 28 | 2,5 | 90 | 20 | 100 | 100 | 100 | 100 | 100 |
| | 1,25 | 50 | 0 | 100 | 100 | 100 | 100 | 100 |
| | 0,625 | 50 | 0 | 100 | 100 | 100 | 100 | 100 |
| 27 | 2,5 | 90 | 20 | 100 | 100 | 100 | 100 | 100 |
| | 1,25 | 50 | 0 | 100 | 100 | 100 | 100 | 100 |
| | 0,625 | 30 | 0 | 100 | 100 | 100 | 100 | 100 |
| 29 | 2,5 | 90 | 40 | 100 | 100 | 100 | 100 | 100 |
| | 1,25 | 80 | 20 | 100 | 100 | 100 | 100 | 100 |
| | 0,625 | 70 | 0 | 100 | 100 | 100 | 100 | 100 |
| 30 | 2,5 | 40 | 20 | 100 | 100 | 100 | 100 | 90 |
| | 1,25 | 20 | 0 | 100 | 100 | 100 | 100 | 90 |
| | 0,625 | 0 | 0 | 100 | 100 | 100 | 100 | 90 |
| 31 | 2,5 | 90 | 20 | 100 | 100 | 100 | 100 | 100 |
| | 1,25 | 80 | 0 | 100 | 100 | 100 | 100 | 100 |
| | 0,625 | 60 | 0 | 100 | 100 | 100 | 100 | 100 |
| 26 | 2,5 | 100 | 80 | 100 | 100 | 100 | 100 | 100 |
| | 1,25 | 60 | 50 | 100 | 100 | 100 | 100 | 100 |
| | 0,625 | 0 | 40 | 100 | 100 | 100 | 100 | 100 |
| 21 | 2,5 | 100 | 90 | 100 | 100 | 100 | 100 | 100 |
| | 1,25 | 100 | 80 | 100 | 100 | 100 | 100 | 100 |
| | 0,625 | 100 | 80 | 100 | 90 | 100 | 100 | 100 |
| 23 | 2,5 | 100 | 80 | 100 | 100 | 100 | 100 | 100 |
| | 1,25 | 100 | 80 | 100 | 100 | 100 | 100 | 100 |
| | 0,625 | 80 | 40 | 100 | 100 | 100 | 100 | 100 |
| 24 | 2,5 | 100 | 80 | 100 | 100 | 100 | 100 | 100 |
| | 1,25 | 100 | 70 | 100 | 100 | 100 | 100 | 100 |
| | 0,625 | 100 | 70 | 100 | 100 | 100 | 100 | 100 |
| 25 | 2,5 | 100 | 80 | 100 | 100 | 100 | 100 | 100 |
| | 1,25 | 100 | 70 | 100 | 100 | 100 | 100 | 100 |
| | 0,625 | 100 | 40 | 100 | 90 | 90 | 100 | 100 |
| 20 | 2,5 | 100 | 80 | 100 | 100 | 100 | 100 | 100 |
| | 1,25 | 100 | 60 | 100 | 100 | 100 | 100 | 100 |
| | 0,625 | 90 | 60 | 100 | 100 | 100 | 100 | 100 |

Table B₂

| Active compound | Pre-emergence Test Amount of active compound used, kg/ha | Beets | Gallinsoga | Matricaria | Stellaria |
|---|---|---|---|---|---|
| (known) structure | 5 | 100 | 100 | 100 | 100 |
| (4) structure | 5 | 0 | 100 | 100 | 100 |

Table B₂-continued

| Active compound | Pre-emergence Test Amount of active compound used, kg/ha | Beets | Gallinsoga | Matricaria | Stellaria |
|---|---|---|---|---|---|
| (10) [structure with CF₃-phenyl, OC₂H₅, C₂H₅] | 5 | 0 | 100 | 90 | 100 |
| (6) [structure with phenyl, OC₄H₉-n, CH₃] | 5 | 0 | 100 | 90 | 100 |

It will be understood that the specification and examples are illustrative but not limitative of the present invention and that other embodiments within the spirit and scope of the invention will suggest themselves to those skilled in the art.

What is claimed is:

1. N-(1,2,4-triazin-5-on-4-yl)-glycine compound of the formula $$R^2-\underset{\underset{N}{\parallel}}{C}-\underset{\underset{N}{\parallel}}{C}(=O)-N(NH-CH(OR^3)-COR^4)-C(R^1)=N-$$

in which
- $R^1$ is alkyl, alkoxy, alkylthio or alkylamino of up to 4 carbon atoms,
- $R^2$ is alkyl of from 1 to 6 carbon atoms, cycloalkyl of from 5 to 7 carbon atoms, phenyl or substituted phenyl, wherein the substituents are selected from halogen, alkyl and alkoxy of up to 2 carbon atoms, haloalkyl and up to 2 carbon atoms and up to 5 halogen atoms, cyano or nitro;
- $R^3$ is hydrogen, alkyl of from 1 to 4 carbon atoms, alkenyl or alkynyl of from 2 to 4 carbon atoms; and
- $R^4$ is hydroxyl, alkoxy or alkylthio of from 1 to 4 carbon atoms, amino or alkylamino or dialkylamino of up to 4 carbon atoms in each alkyl moiety.

2. N-(1,2,4-triazin-5-on-4-yl)-glycine compound as claimed in claim 1 wherein $R^1$ is alkyl of up to 4 carbon atoms.

3. N-(1,2,4-triazin-5-on-4-yl glycine compound as claimed in claim 1 wherein $R^1$ is alkoxy or alkylthio of from 1 to 4 carbon atoms.

4. N-(1,2,4-triazin-5-on-4-yl)-glycine compound as claimed in claim 1 wherein $R^1$ is alkylamino of from 2 to 4 carbon atoms.

5. N-(1,2,4-triazin-5-on-4-yl)-glycine compound as claimed in claim 1 wherein $R^2$ is alkyl of up to 6 carbon atoms.

6. N-(1,2,4-triazin-5-on-4-yl)-glycine compound as claimed in claim 1 wherein $R^2$ is tert. butyl.

7. N-(1,2,4-triazin-5-on-4-yl)-glycine compound as claimed in claim 1 wherein $R^2$ is cycloalkyl of 5 to 7 carbon atoms.

8. N-(1,2,4-triazin-5-on-4-yl)-glycine compound as claimed in claim 1 wherein $R^2$ is phenyl.

9. N-(1,2,4-triazin-5-on-4-yl)-glycine compound as claimed in claim 1 wherein $R^2$ is phenyl substituted with halogen, alkyl or alkoxy of up to 2 carbon atoms, haloalkyl of up to 2 carbon atoms, cyano or nitro.

10. N-(1,2,4-triazin-5-on-4-yl)-glycine compound as claimed in claim 1 wherein $R^3$ is hydrogen.

11. N-(1,2,4-triazin-5-on-4-yl)-glycine compound as claimed in claim 1 wherein $R^3$ is alkyl of up to 4 carbon atoms.

12. N-(1,2,4-triazin-5-on-4-yl)-glycine compound as claimed in claim 1 wherein $R^3$ is alkenyl or alkynyl of up to 4 carbon atoms.

13. N-(1,2,4-triazin-5-on-4-yl)-glycine compound as claimed in claim 1 wherein $R^4$ is hydroxyl.

14. N-(1,2,4-triazin-5-on-4-yl)-glycine compound as claimed in claim 1 wherein $R^4$ is alkoxy or alkylthio of up to 4 carbon atoms.

15. N-(1,2,4-triazin-5-on-4-yl)-glycine compound as claimed in claim 1 wherein $R^4$ is amino, alkylamino or dialkylamino of up to 4 carbon atoms in each alkyl moiety.

16. N-(1,2,4-triazin-5-on-4-yl)-glycine compound as claimed in claim 1 wherein $R^4$ is methoxy or ethoxy.

17. N-(1,2,4-triazin-5-on-4-yl)-glycine compound as claimed in claim 1 designated N-(3-methylthio-6-tert.-butyl-1,2,4-triazin-5-on-4-yl)-α-ethoxy-glycine.

18. N-(1,2,4-triazin-5-on-4-yl)-glycine compound as claimed in claim 1 designated N-(3-methylthio-6-tert.-butyl-1,2,4-triazin-5-on-4-yl)-α-methoxy-glycine.

19. N-(1,2,4-triazin-5-on-4-yl)-glycine compound as claimed in claim 1 designated N-(3-methylthio-6-tert.-butyl-1,2,4-triazin-5-on-4-yl)-α-isopropoxy-glycine.

20. N-(1,2,4-triazin-5-on-4-yl)-glycine compound as claimed in claim 1 designated N-(3-isopropyl-6-tert.-butyl-1,2,4-triazin-5-on-yl)-α-isopropoxy-glycine.

21. Herbicidal compositions comprising a herbicidally acceptable carrier and in effective amount an N-(1,2,4-triazin-5-on-4-yl)-glycine compound as claimed in claim 1.

22. Method of combating undesired vegetation which method comprises applying to such vegetation or its habitat a herbicidally effective amount of an N-(1,2,4-triazin-5-on-4-yl)-glycine compound of the formula:

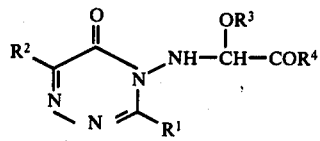

in which
R[1] is alkyl, alkoxy, alkylthio or alkylamino of up to 4 carbon atoms,
R[2] is alkyl of from 1 to 6 carbon atoms, cycloalkyl of from 5 to 7 carbon atoms, phenyl or substituted phenyl, wherein the substituent are selected from halogen, alkyl and alkoxy of up to 2 carbon atoms, haloalkyl of up to 2 carbon atoms and up to 5 halogen atoms, cyano or nitro;
R[3] is hydrogen, alkyl of from 1 to 4 carbon atoms, alkenyl or alkynyl of from 2 to 4 carbon atoms; and
R[4] is hydroxyl, alkoxy or alkylthio of from 1 to 4 carbon atoms, amino or alkylamino or dialkylamino of up to 4 carbon atoms in each alkyl moiety.

23. Method as claimed in claim 22 wherein said compound is applied to an area of agriculture in an amount of 0.1 to 20 kg per hectare.

24. Method as claimed in claim 22 wherein said active compound is applied as a selective herbicide for combating weeds in an area of crop plant cultivation.

25. Method as claimed in claim 24 wherein the crop plants are soy beans, potatoes, cereals, rice or beats.

26. Method as claimed in claim 22 wherein said compound is at least one of the group consisting of N-(3-methylthio-6-tert.-butyl-1,2,4-triazin-5-on-4-yl)-α-ethoxy-glycine, N-(3-methylthio-6-tert.-butyl-1,2,4-triazin-5-on-4-yl)-α-methoxy-glycine, N-(3-methylthio-6-tert.-butyl-1,2,4-triazin-5-on-4-yl)-α-isopropoxy-glycine, and N-(3-isopropyl-6-tert.-butyl-1,2,4-triazin-5-on-4-yl)-α-isopropoxy-glycine.

* * * * *